United States Patent [19]

Shaw et al.

[11] Patent Number: 4,933,062

[45] Date of Patent: Jun. 12, 1990

[54] MODIFIED COMPOSITE ELECTRODES WITH RENEWABLE SURFACE FOR ELECTROCHEMICAL APPLICATIONS AND METHOD OF MAKING SAME

[75] Inventors: Brenda R. Shaw; Kenneth E. Creasy, both of Storrs, Conn.

[73] Assignee: University of Connecticut, Storrs, Conn.

[21] Appl. No.: 320,233

[22] Filed: Mar. 7, 1989

[51] Int. Cl.$^5$ ............................................. C25B 11/04
[52] U.S. Cl. .................................. 204/291; 204/292; 204/294; 429/42; 429/43
[58] Field of Search .................... 204/290 R, 291, 292, 204/294, 280; 429/42, 43

[56] References Cited

U.S. PATENT DOCUMENTS

| | | | |
|---|---|---|---|
| 3,385,780 | 5/1968 | Feng ..................................... | 204/294 |
| 3,533,929 | 10/1970 | Evans et al. ........................ | 204/294 |
| 4,278,525 | 7/1981 | Gestaut ............................... | 204/294 |
| 4,337,140 | 6/1982 | Solomon ............................. | 204/294 |
| 4,339,322 | 7/1982 | Balko et al. ........................ | 204/294 |
| 4,343,767 | 8/1982 | Long et al. ......................... | 204/294 |
| 4,459,324 | 7/1984 | Gauger et al. .................. | 204/290 R |
| 4,461,691 | 7/1984 | Frank .............................. | 204/290 R |
| 4,472,257 | 9/1984 | Sklyaron et al. ................... | 204/294 |
| 4,476,003 | 10/1984 | Frank et al. .................... | 204/290 R |

FOREIGN PATENT DOCUMENTS

| | | | |
|---|---|---|---|
| 1151108 | 8/1983 | Canada . | |
| 45-41003 | 12/1970 | Japan ................................. | 204/294 |

OTHER PUBLICATIONS

H. L. Dickstein, "Preparation of Carbon Black-–Polymer Composites", University of Mass., Ph. D. Thesis, 1987.

J. Chang et al., "Electro-Copolymerization of Acrylonitrile and Methyl Acrylate onto Graphite Fibers", Journal of Applied Polymer Science, vol. 34, 2105–2124 (1987).

R. V. Subramanian et al., "Electrodesposition of a Polymer Interphase in Carbon-Fiber Composites", Polymer Composites, Aug. 1986, vol. 7, No. 4, pp. 201–218.

R. V. Bramanian et al., "Electropolymerization on Graphite Fibers", Polymer Engineering Science, May 1978, vol. 18, No. 7, pp. 590–600 (1978).

J. Golas et al., "Carbon-Fiber Micro-Electrodes as Substrates for Mercury Films", Analytica Chimica Acta, 186 (1986), pp. 1–9.

Fathalla Belal et al., "Flow Injection Alalysis of Three N–Substituted Phenothiazine Drugs with Amperometric Detection at a Carbon Fibre-Array Electrode", Analyst, Dec. 1985, vol. 110, pp. 1493–1496.

Lipka et al., "The Electrochemical Behavior of Graphite Fiber-Epoxy Composite Electrodes Containing Varying Fiber Orientations", Electrochemical Science and Technology, Feb. 1988, pp. 368–372.

Neal Sleszynski et al., "Arrays of Very Small Voltammetric Electrodes Based on Reticulated Vitreous Carbon", Analytical Chemistry, vol. 56, No. 2, Feb. 1984, pp. 130–135.

C. Amatore et al., "Charge Transfer at Partially Blocked Surfaces, A Model for the Case of Microscopic Active and Inactive Sites", J. Electroanal Chemistry, #147, 1983, pp. 39–51.

Duane Welsshaar et al., "Kel-F-Graphite Composite Electrode as an Electrochemical Detector for Liquid Chromatography and Application to Phenolic Compounds", Alalytical Chemistry, 1981, #53, pp. 1809–1813.

J. Redepenning, "Chemically Modified Electrodes: A General Overview Trends in Analytical Chemistry", vol. 6, No. 1, 1987, pp. 18–22.

L. Santos et al., "Electrochemistry and Chromatographic Detection of Monosaccharides, Disaccharieds, and Related Compounds at an Electrocatalytic Chemically Modified Electrode", Analytica Chimica Acta, 206 (1988), pp. 85–96.

*Primary Examiner*—John F. Niebling
*Assistant Examiner*—Kathryn Gorgos

[57] ABSTRACT

Renewable modified composite electrodes for electrochemical application are provided by homogeneous structure of a conductive filler disposed in a polymeric matrix or binder containing a modifier in the polymer chain. The modifier provides distinctive characteristics of electroactivity, inclusion, acidic/basic, complexing/chelating or electrocatalysis to the surface of the electrode in a solution. After use, the electrode may be renewed by removing a surface portion and thereby exposing a fresh portion of the homogeneous structure.

10 Claims, No Drawings

MODIFIED COMPOSITE ELECTRODES WITH RENEWABLE SURFACE FOR ELECTROCHEMICAL APPLICATIONS AND METHOD OF MAKING SAME

BACKGROUND OF THE INVENTION

The present invention relates to renewable modified composite electrodes for electrochemical applications and to methods for making same.

Modified electrodes have become of great interest because of their ability to extend the range of characteristics provided by the intrinsic interfacial properties of traditional electrodes. Such electrodes have become important tools in electroanalytical chemistry and the uses have been expanding as new modifiers have been identified.

Heretofore, such electrodes have been prepared by application to the surface of an electrode a coating of a modifier to provide the desired disused alteration of the surface characteristics. In many applications, the surface layer becomes contaminated or attacked by the solution in which the electrode is immersed so that the modified electrode may not be reused. Moreover, the coating may not be uniform and thus produce variation in activity over the surface of the electrode. Thus, substitution of another electrode may involve some change in electrode characteristics and introduce problems of reproducibility of results.

It is an object of the present invention to provide a novel modified composite electrode which may be renewed by removing a surface portion thereof.

It is also an object to provide such an electrode which is homogeneous throughout its cross section and which may provide multiple forms of modification.

Another object is to provide a novel method for preparing such modified composite electrodes and for renewing such electrodes.

SUMMARY OF THE INVENTION

It has now been found that the foregoing and related objects and advantages may be readily attained in a renewable composite electrode for electrochemical applications which is formed from a composition which contains 1–99 percent by weight of a non-conductive polymeric matrix with a modifier in the polymer chain. Disposed within the matrix is 1–99 percent by weight of a conductive filler sufficient to provide electrical conductivity in the electrode. The modifier provides to the electrode distinctive properties selected from the group consisting of electroactivity, inclusion, acidic basic, complexing/chelating, and electrocatalysis. This electrode is renewable by removal of a surface portion thereof to expose a fresh portion thereof.

The modifier is an organic material which may be copolymerizable with a polymerizable monomer to form the polymeric matrix, or it may cross-link with a polymeric substrate to form the polymeric matrix.

For some applications, the modifier produces a polymer which exhibits such properties only upon application of a potential to the electrode. In another application, the modifier produces a polymer which exhibits properties which will enable measurement of the potential of a solution in which immersed at zero current. In the making of such composite electrodes, there is produced an admixture of 1–99 parts by weight of a conductive filler and 1–99 parts by weight of a reactive polymeric matrix material containing a modifier which produces a polymer matrix adapted to impart to the electrode such distinctive properties. The admixture is subjected to conditions to react the matrix material and convert the admixture into a solid structure of homogeneous composition in which the filler is dispersed within the matrix polymer and thereby forms an electrode.

DETAILED DESCRIPTION OF THE INVENTION

The electrodes of the present invention are composites in that they are fabricated from a conductive filler in a resin matrix or binder to produce the desired conductivity, strength and surface properties. They are modified in that they utilize modifiers to impart the desired surface characteristics in the solution in which immersed.

The conductive fillers may be particulate such as carbon black, graphite and metal powders, fibrous such as carbon fibers, or metallic wire. The fillers not only provide conductivity to the composite structure but fibrous fillers also contribute to the strength, dimensional stability and other physical properties of the electrode. Generally, the particulates will have a particle size of 10–1000 millimicrons to provide good dispersability. The fibers or wires will normally have a diameter of about 0.1–100 nanometers and preferably 5–50 nanometers, and a length of at least 2 millimeters and up to the length of the electrode.

The polymeric matrix or binder is an interpolymer or cross-linked polymer in which the modifier is disposed along the length of the polymer chain, generally as a branch or in some other structural position in which its functional component is available for interaction with the component(s) of the solution in which immersed. The polymer should provide the composite with its dimensional stability and other desired properties such as resistance to excessive attack by the solution in which immersed. Exemplary of suitable monomers are vinyl monomers such as styrenes and acrylics; the polymers may be interpolymers and cross-linked polymers offer a high degree of stability.

Composite electrodes comprising a conductive filler and a polymer binder or matrix are known in the art. Generally, depending upon the filler and resins selected and the desired conductivity (or resistivity, the filler will comprise 1–99 percent by weight of the composition, and the matrix polymer will comprise 1–99 percent by weight. Most usually, a particulate filler will comprise 5–15 percent by weight, and the matrix polymer is 85–95 percent by weight of the composition with fibrous fillers in which higher percentages may be employed because they do not embrittle the matrix polymer.

The modifier (or modifiers) to be incorporated in the polymer will depend upon the property or properties which are desired for the surface of the electrode. As has been previously indicated, one or more modifiers are included in an amount sufficient to impart the desired properties. Depending upon the modifier selected, the filler and the resinous components, the modifier may comprise 1–50 percent by weight of the polymer and usually it will comprise 2–20 percent by weight.

The distinctive properties imparted by the modifier offer the opportunity to utilize such renewable electrodes for various electrochemical applications, and the properties attributable to such modifiers will be recognized by those familiar with electrochemistry and electroanalytical techniques.

Electroactivity is generally considered to be the ability to oxidize or reduce the modifier when it is disposed at the surface of an electrode in contact with a solution or other medium in which it is disposed. Such modifiers may be used as electrocatalysts, as mediators, as sources of reference potentials, and as sensors of the redox potential of the surrounding solution. Exemplary of such materials is vinylpyridine.

Inclusion is generally considered to be the ability to incorporate species from the surrounding solution by ion exchange or other host-guest interactions. Such modifiers may be used as an electrocatalyst, as a support for an electrocatalyst, as a means to concentrate species from the surrounding medium, as a means of delivering species to the solution in the region surrounding the surface of the electrode, and as a potentiometric sensor for species which may be incorporated at internal or surface sites. Exemplary of such modifiers are polymeric materials with ion exchange properties and coordinating compounds.

Adsorption is generally considered to be the ability to adsorb species from the surrounding solution by or other surface interactions. Such modifiers may be used as electrocatalysts, as supports for electrocatalysts, as means to concentrate species from the surrounding medium, and as a potentiometric sensor for species which are adsorbed at surface sites.

Electrocatalysis is generally considered to be the ability to enhance the current for oxidation or reduction of some species in solution at a given potential relative to a similar electrode without the modifier. Exemplary of such materials is vinylferrocene which can catalyze oxidation of ascorbic acid.

Acidic/basic is generally considered to be the ability to alter the pH of the electrode surface when immersed in the solution. Exemplary of such materials is co-poly(vinylpyridine) which can be protonated in a highly acidic solution.

Complexing/chelating is generally considered to be the ability to complex or chelate ions at the surface of the electrode when immersed in solution. Exemplary of such materials are co-poly(vinylpyridine) and monomeric forms of phenanthrolines and other coordinating or chelating ligands.

Some modifiers may exhibit properties in more than one class of activity, or different properties in different solutions or at different pH or at different applied potentials. Moreover, modified electrodes may utilize more than one type of modifier where multiple effects are desired.

The size and thickness$s of the electrode formed from the composition will depend upon the application, but they should be sufficient to permit its renewal by removal of the contaminated or altered surface portion. The amount of surface to be removed will depend upon the type of contamination or alteration. Generally, removal of 2–10 nanometers is required, and amounts of up to 100 nanometers may be required if the surface has been swollen by the solution. Removal of the surface may be effected by fine polishing for followed by rinsing, or by slicing off a surface layer, or by any other suitable technique. The electrode should then be thoroughly washed.

Such modified electrodes may have applications in various areas of technology where this surface modification improves the electrochemical activity. Electroanalysis is a particularly fertile application. Other applications include sensors and detectors. Moreover, such electrodes present an opportunity to improve apparatus using electrochemical activity such as fuel cells and batteries.

Several different methods for making the electrodes may be employed. A cross linking agent modifier may be thoroughly admixed with a comonomer or prepolymer and then these components are thoroughly admixed and then admixed with the filler, after which the composition is disposed in molds or extruded under conditions which will convert the resinous components into a solid binder or matrix for the filler.

The particular technique utilized will generally depend upon the resin formulation and the modifier. Where polymerization is the principal mechanism being employed, and an initiator incorporated, preliminary admixture is generally preferable.

Following formation of the electrodes, they are desirably polished to a smooth surface. This may involve initial coarse sanding followed by polishing with a fine grit material.

Exemplary of the present invention are the following specific examples.

EXAMPLE ONE

Electrodes are formed from a thoroughly dispersed disposed admixture of 71 parts styrene, 20 parts of technical grade divinylbenzene, 2.5 parts vinylferrocene, 0.5 part of 2,2'-azobis(2-methylpropionitrile) (AIBN). The monomers and AIBN were initially admixed and 6 parts Ketjenblack were thoroughly dispersed by sonication for 20 minutes. The composition was placed in glass tubes of 3 mm. inside diameter which were then heated in an oven for 6–24 hours at 65° C. Upon solidification and cooling, a gap was formed due to differences in thermal expansion; this was filled with fresh composition and the tubes were again heated to polymerize the fresh composition. The resultant cylindrical electrodes were then removed from the tubes, polished by hand and thoroughly rinsed.

The resultant electrodes did not crumble when broken indicating complete encapsulation of the graphite particles.

Testing of the electrodes in a lithium perchlorate solution (0.5 M) electrolyte produced voltammograms, which showed sharp anodic peaks and broad cathodic peaks indicating high electroactivity.

Although some surface swelling was observed when the electrodes were tested in acetonitrile, the polymer did not dissolve, and the glassy surface could be renewed by polishing to remove the swollen surface portion.

EXAMPLE TWO

Electrodes were similarly prepared from 42.7 parts styrene, 33.6 parts of technical grade divinylbenzene, 17.4 parts vinylpyridine, 1.1 parts AIBN, and 5.2 parts carbon black. The surfaces of the electrodes were smooth, and the electrodes did not crumble when broken.

In testing of modified composite electrodes using the above formulation and similarly prepared electrodes containing a different monomer mixture (18.6 DVB, 37.1 styrene, and 38.2 vinylpyridine), they were immersed in aqueous solutions containing ferricyanide ions. The modified electrodes of the present invention demonstrated enhanced sensitivity with respect to unmodified electrodes and the surface of the electrodes appeared to swell as a result of the apparent chelation.

Thus, it can be seen from the foregoing detailed specification and examples that the modified composite electrodes of the present invention provide highly effective electrodes with surfaces which enhance electrochemical applications. They may be fabricated relatively easily and at relatively low cost, and they may be readily renewed by removing the contaminated or affected surface.

We claim:

1. A self-supporting renewable modified composite electrode for electrochemical applications comprising substantially homogeneous structure of a composition consisting of:
   (a) 1-99 percent by weight of a non-conductive polymeric matrix having a polymer-chain in which a modifier is dispersed and
   (b) 1-99 percent by weight of a conductive filler dispersed throughout said matrix and sufficient to provide electrical conductivity in the electrode, said modifier providing to said electrode distinctive properties selected from the group consisting of electroactivity, inclusion, acidic/basic, complexing/chelating, and electrocatalysis, said body being formed by polymerization of a resinous composition with said filler dispersed therein, said electrode being homogeneous throughout its cross section so that the electrode is renewable by removal of a surface portion to expose a fresh portion thereof.

2. The electrode in accordance with claim 1 wherein said modifier is copolymerizable with a polymerizable monomer to form said polymeric matrix.

3. The electrode in accordance with claim 1 wherein said modifier is a cross linking agent cross linked with a polymeric substrate to form said polymeric matrix.

4. The electrode in accordance with claim 1 wherein said modifier is non-conductive.

5. The electrode in accordance with claim 1 wherein said modifier exhibits such properties only upon application of a potential to said electrode.

6. The electrode in accordance with claim 1 wherein said modifier exhibits properties which will enable measurement of the potential of a solution in which immersed at zero current.

7. The electrode in accordance with claim 1 wherein said modifier exhibiting electroactive properties is selected from the group consisting of organic compounds polymers, and metallo-organic compounds.

8. The electrode in accordance with claim 1 wherein said modifier is one exhibiting inclusion properties and is adapted to incorporate species from a solution in which immersed and which is selected from the group which will produce polymers with ion exchange and coordinating agent properties.

9. The electrode in accordance with claim 1 wherein said modifier is non-conductive and enhances electroactivity upon application of a potential to the electrode in a solution.

10. The electrode in accordance with claim 1 wherein said polymeric matrix comprises 80-95 percent by weight of the composite electrode.

* * * * *